United States Patent
Iwahara et al.

(10) Patent No.: US 9,095,143 B2
(45) Date of Patent: Aug. 4, 2015

(54) ANTIMICROBIAL AGENT AND METHOD FOR PRODUCING THE SAME

(75) Inventors: Masayoshi Iwahara, Kumamoto (JP);
Hiroshi Morita, Fukuoka (JP);
Kazuyuki Miyata, Kumamoto (JP)

(73) Assignee: KABUSHIKI KAISHA OUJU SEIYAKU, Kumamoto (JP)

( * ) Notice: Subject to any disclaimer, the term of this patent is extended or adjusted under 35 U.S.C. 154(b) by 0 days.

(21) Appl. No.: 14/232,472

(22) PCT Filed: Jul. 13, 2012

(86) PCT No.: PCT/JP2012/004547
§ 371 (c)(1),
(2), (4) Date: Jan. 13, 2014

(87) PCT Pub. No.: WO2013/011679
PCT Pub. Date: Jan. 24, 2013

(65) Prior Publication Data
US 2014/0134153 A1    May 15, 2014

(30) Foreign Application Priority Data

Jul. 15, 2011    (JP) .................................. 2011-156607

(51) Int. Cl.
| | | |
|---|---|---|
| *A61K 35/00* | (2006.01) | |
| *A01N 63/02* | (2006.01) | |
| *C12N 1/14* | (2006.01) | |
| *C12P 1/02* | (2006.01) | |
| *A01N 63/00* | (2006.01) | |
| *A61K 36/88* | (2006.01) | |
| *A61K 36/185* | (2006.01) | |
| *A61K 36/07* | (2006.01) | |
| *A61K 36/074* | (2006.01) | |

(52) U.S. Cl.
CPC ................ *A01N 63/02* (2013.01); *A01N 63/00* (2013.01); *A61K 36/07* (2013.01); *A61K 36/074* (2013.01); *A61K 36/185* (2013.01); *A61K 36/88* (2013.01); *C12N 1/14* (2013.01); *C12P 1/02* (2013.01); *A61K 2236/19* (2013.01)

(58) Field of Classification Search
None
See application file for complete search history.

(56) References Cited

U.S. PATENT DOCUMENTS 6,726,911 B1 *    4/2004    Julich et al. ............... 424/195.15

FOREIGN PATENT DOCUMENTS

| JP | H1160423 A | 3/1999 |
|---|---|---|
| JP | H1160424 A | 3/1999 |
| JP | 2002249436 A | 9/2002 |
| JP | 2003310254 A | 11/2003 |
| JP | 2006181901 A | 7/2006 |
| JP | 2007-001961 A | 1/2007 |

OTHER PUBLICATIONS

Oyaizu et al., The of the Japan Oil Chemists' Society, 1991, 40(6), 511-515, Abstract Only.*

* cited by examiner

*Primary Examiner* — Kade Ariani
(74) *Attorney, Agent, or Firm* — Marshall, Gerstein & Borun LLP

(57) ABSTRACT

A method for producing an antimicrobial agent, by cutting, or cutting and then milling a plant belonging to the family Juncaceae: mixing the cut plant with a nutrient source for a seed culture of mushroom mycelia, to form a mixture; inoculating the seed culture of mycelia to the mixture of the plant belonging to the family Juncaceae and the nutrient source and then culturing the seed culture at a growth temperature for the seed culture of mycelia to produce the antimicrobial agent.

20 Claims, 12 Drawing Sheets

Antifungal effect of antimicrobial agent made from rush, Mannentake and soybean curd refuse against *Fusarium oxysporum* (colony counting)

Antifungal effect of antimicrobial agent
made from rush, Mannentake and soybean
curd refuse against *Fusarium oxysporum*
(colony counting)

Antifungal effect of antimicrobial agent
made from rush, Mannentake and soybean
curd refuse against *Fusarium oxysporum*
(Standard growth score)

Antifungal effect of antimicrobial agent
made from rush, Mannentake and soybean
curd refuse against
*Cladosporium cladosporioides*
(colony counting)

Antifungal effect of antimicrobial agent
made from rush, Mannentake and soybean
curd refuse against
*Cladosporium cladosporioides*
(Standard growth score)

Antifungal effect of functional food
made from rush, Mannentake and soybean
curd refuse against
*Trichophyton violaveum*
(colony counting)

Antifungal effect of antimicrobial agent
made from rush, Mannentake and
soybean curd refuse against
*Trichophyton violaceum*
(Standard growth score)

Antifungal effect of antimicrobial agent
made from rush, Mannentake and soybean
curd refuse against *Microsporum canis*
(colony counting)

Antifungal effect of antimicrobial agent
made from rush, Mannentake and soybean
curd refuse against *Microsporum canis*
(Standard growth score)

Bactericidal effect of antimicrobial
agent made from rush, Mannentake and
soybean curd refuse against
*Escherichia coli*

Bactericidal effect of antimicrobial
agent made from rush, Mannentake and
soybean curd refuse against
*Bacillus subtilis*

Bactericidal effect of antimicrobial
agent made from rush, Mannentake and
soybean curd refuse against
*Staphylococcus aureus*

Bactericidal effect of antimicrobial
agent made from rush, Mannentake and
soybean curd refuse against
*Micrococcus luteus*

ANTIMICROBIAL AGENT AND METHOD FOR PRODUCING THE SAME

TECHNICAL FIELD

The present invention relates to an antimicrobial agent containing as main raw materials a plant belonging to the family Juncaceae such as edible rush and a mycelium of mushroom such as Mannentake/Reishi (*Ganoderma lucidum*) and a method for producing the same. The antimicrobial agent of the present invention can be used for food, can be used as an agricultural chemical for plants, can be applied to a plant rhizosphere as a soil conditioner, can be used as a therapeutic agent for athlete's foot and can be used as an antimicrobial agent for hands and fingers.

BACKGROUND ART

Rush, which is used as a raw material of tatami (straw mat) in Japan, is a perennial plant classified in the genus *Juncus* and also known as a herbal medicine called as Toshinso (*Juncus decipiens*). Rush has no toxicity and is said to have efficacy as a medical plant for an antimicrobial drug, a diuretic drug, an anti-inflammatory drug, a tranquilizer drug and a drug for insomnia. In addition, it is found that rush has an antimicrobial activity against food poisoning bacteria and putrefactive bacteria. Further, rush has an antimicrobial activity against putrefactive bacteria: *Bacillus subtilis* and *Micrococcus* sp. as well as food poisoning bacteria: *Salmonella* sp. *Staphylococcus aureus* and enterohemorrhagic *Escherichia coli* O157, O26 and O111. And on the lab-scale, rush with a concentration of around 1 to 10% exerts these antimicrobial activities (for example, see Patent Document 1).

Besides, as a method for producing an enzyme which utilizes a plant as a substrate, proposed is a production method of an enzyme using rush in that rush which has been at least washed with water is powdered, and this rush powder is sterilized and used as a culture substrate to culture filamentous fungi (for example, see Patent Document 2).

According to Patent Document 1, it is revealed that a growth inhibitory effect against mold can be obtained by heating rush in an alkaline solution with pH of 9 or more. This treatment enables rush to be used as a rush material added with a growth inhibitory effect against mold for, for example, building materials and other materials relating to housing; papers; clothing materials; packaging materials relating to food; and the like. In addition, it is also possible to use rush as it is after the alkaline treatment without being washed with water for the purpose of growth inhibition of mold. In this case, it is disclosed that a growth control effect against mold by pH can also be added in addition to a growth inhibitory effect against mold that rush has, which further enhances a growth inhibitory effect of rush against mold.

According to Patent Document 2, rush is used as a substrate when producing a useful enzyme by culturing filamentous fungi. Since rush has a porous and sponge-like inner structure, the inside of rush contains a large amount of air, which is a suitable environment for aerobic microorganisms. Specifically, cut and dried rush is washed with water to remove attached substances, and the rush is further dried and then milled into powder. A required amount of pure water and pectin is added to the rush powder, and the mixture is sterilized by heating and then cooled to room temperature, thereby obtaining a culture substrate. This substrate serves as a medium having a bread-like structure containing moisture. A microorganism to be cultured, for example, filamentous fungi (liquid) which is mold is inoculated to the medium and cultured for several days while maintaining a predetermined temperature. In this case, the microorganism is cultured, for example, over 7 to 30 days or more depending on the kind of the microorganism cultured.

PRIOR ART DOCUMENTS

Patent Documents

Patent Document 1: JP 2006-1891901 A
Patent Document 2: JP 2003-310254 A

SUMMARY OF THE INVENTION

Problems to be Solved by the Invention

Although Patent Document 1 describes that rush has an antimicrobial activity against food poisoning bacteria and putrefactive bacteria, rush is used as a material for housing and clothing.

Patent Document 2 describes a method for producing a useful enzyme by using rush as a culture substrate to which mold is inoculated. However, mushroom mycelium is not inoculated and there is no description about producing an antimicrobial agent and adding a nutrient source for the mycelium.

On the other hand, an object of the present invention is to provide an antimicrobial agent which utilizes an antimicrobial activity and a pharmacological activity of a plant belonging to the family Juncaceae, contains a material produced by seeding a seed culture of mushroom mycelia to a plant belonging to the family Juncaceae, culturing the mycelium while adding a nutrient source to thereby proliferate the mycelium and then drying the proliferated mycelium, can exhibit an excellent antimicrobial activity even when used in a small amount, can be added to a food, can be added to fish bait, can be sprayed onto an agricultural crop or soil, and can be used as a therapeutic agent for athlete's foot; and a method for producing the antimicrobial agent.

Solutions to the Problems

In order to solve the above-mentioned problems, the method for producing an antimicrobial agent relating to the present invention is characterized in that a plant belonging to the family Juncaceae (suitably treated when used for a food: one washed with water to remove attached substances from the plant) which plant is cut into a predetermined length or milled is mixed with a nutrient source for a seed culture of mushroom mycelia, and the seed culture of mycelia is inoculated to the mixture of the plant belonging to the family Juncaceae and the nutrient source and then cultured at a growth temperature for the seed culture of mycelia for a predetermined time period.

According to the method for producing an antimicrobial agent relating to the present invention, the seed culture of mushroom mycelia seeded to the plant belonging to the family Juncaceae and the nutrient source is cultured to proliferate while taking the nutrient source. The mycelium mainly penetrates inside of the plant belonging to the family Juncaceae, and proliferates while taking the nutrient source. Since the mycelium penetrates inside of the plant belonging to the family Juncaceae, and proliferates, the antimicrobial agent relating to the present invention exerts an antimicrobial activity, an antimicrobial activity and an antiseptic activity of the mycelium synergistically along with a pharmacological activity, an antimicrobial activity and the like of the plant belonging to the family Juncaceae. Therefore, an antimicrobial activity, an antiseptic activity or an antimicrobial activity is largely improved compared with a case of culturing a seed culture of mushroom mycelia alone to proliferate, which results in high antibacterial and antiseptic effects of the produced antimicrobial agent in a small amount.

As described in claim 2, the plant belonging to the family Juncaceae may be at least one plant selected from rush (I, Toshinso (*Juncus decipiens*), beeg), Kohige, Hosoi, Inui (*Juncus yokoscensis*), Ezohosoi, Itoi (*Juncus maximowiezii* Buchen), Miyamai, Takanei, Hanabizekisho and Kusai (*Juncus tenuis*).

As described in claim 3, the seed culture of mycelia may be at least one Basidiomycete mycelium selected from Mannentake/Reishi (*Ganoderma lucidum*), Meshimakobu (*Fomes yucatensis*), Yamabushitake (*Hericium erinaceum*), Jew's ear mushroom (*Auricularia auricula-judae*), Tamogitake (*Pleurotus citrinopileatus*), Shiitake mushroom (*Lentinus edodes*) and *Agaricus* (Himematsutake) (*Agaricus subrufescens*).

As described in claim 4, the nutrient source may be at least one selected from okara (soybean curd refuse), wheat bran, rice bran, sake lees (shochu (Japanese distilled liquor) distillation residue) and soybean broth (cooking liquid of soy bean).

As described in claim 5, it is desirable that the plant belonging to the family Juncaceae be rush, the seed culture of mycelia be Mannentake (one kind of Ganodermataceae, Reishi), and the nutrient source be okara (soybean curd refuse).

According to the thus selected and produced antimicrobial agent, although rush itself has an excellent antimicrobial activity, Mannentake mycelium also penetrates inside of the honeycomb structure of rush and the mycelium proliferates while taking okara (soybean curd refuse) as a nutrient source. Thus proliferated mycelium has a strong antimicrobial activity and a strong antimicrobial activity, and the antibacterial, antimicrobial and antiseptic activities are exerted synergistically along with the antimicrobial activity of rush. Therefore, the antimicrobial agent exerts excellent antibacterial and antiseptic activities with a very small amount. Moreover, the antimicrobial agent is harmless to foods and crops and can be used as a food antiseptic agent and a disinfectant agent for crops.

As described in claim 6, in the method for producing an antimicrobial agent according to claim 5, it is desirable that the mixture be sterilized by autoclaving at 121° C. for 60 to 90 minutes and cooled, and then the seed culture of mycelia be inoculated to the mixture and cultured at a temperature of 20 to 30° C. for 1 to 3 months or longer.

As described in claim 7, in the method for producing an antimicrobial agent according to claim 5, it is desirable that the mixing ratio (the weight ratio) of the mixture be 0.5 to 1.5 of okara (soybean curd refuse) to 0.5 to 1.5 of rush, the mixture be sterilized by autoclaving and then Mannentake mycelium be inoculated in an amount of 1 to 10% of the total weight of the mixture.

The water-soluble antimicrobial agent according to claim 8 is characterized by containing a filtrate or a concentrate of the filtrate, which filtrate is obtained by filtrating a water extract of a dried material of an antimicrobial agent produced by the production method according to any one of claims 5 to 7.

The powdered antimicrobial agent according to claim 9 is characterized by finely milling a dried material of an antimicrobial agent produced by the production method according to any one of claims 5 to 7.

This makes the antimicrobial agent in a powdered form, which is easy to handle.

The powdered antimicrobial agent according to claim 10 is characterized by finely milling a dried material residue obtained after extracting a dried material of an antimicrobial agent produced by the production method according to any one of claims 5 to 7 with water or by finely milling the dried material residue with the dried material.

This also makes it possible to utilize the residue left after water extraction as an antimicrobial agent, which saves waste and is economical.

Effects of the Invention

As described above, according to the antimicrobial agent relating to the present invention, the seed culture of mycelia seeded to the plant belonging to the family Juncaceae and the nutrient source is cultured to proliferate while taking the nutrient source. The mycelium mainly penetrates inside of the plant belonging to the family Juncaceae, and proliferates taking the nutrient source. Since the mycelium penetrates inside of the plant belonging to the family Juncaceae, and proliferates, the antimicrobial agent relating to the present invention exerts an antimicrobial activity, an antimicrobial activity and an antiseptic activity of the mycelium synergistically along with a pharmacological activity, an antimicrobial activity and the like of the plant belonging to the family Juncaceae. Therefore, an antimicrobial activity, an antiseptic activity or an antimicrobial activity is largely improved compared with a case of culturing a seed culture of mycelia alone to proliferate, which results in high antibacterial and antiseptic effects of the produced antimicrobial agent in a small amount.

Mixing the antimicrobial agent relating to the present invention with partial-dried solid bait (moist pellet) for cultured fish makes the bait less perishable, which prevents environmental pollution caused by bait left uneaten in a sea area surrounding an aquaculture area and especially prevents the development of the red tide caused by eutrophication of the sea area.

EMBODIMENTS OF THE INVENTION

Figure 1:
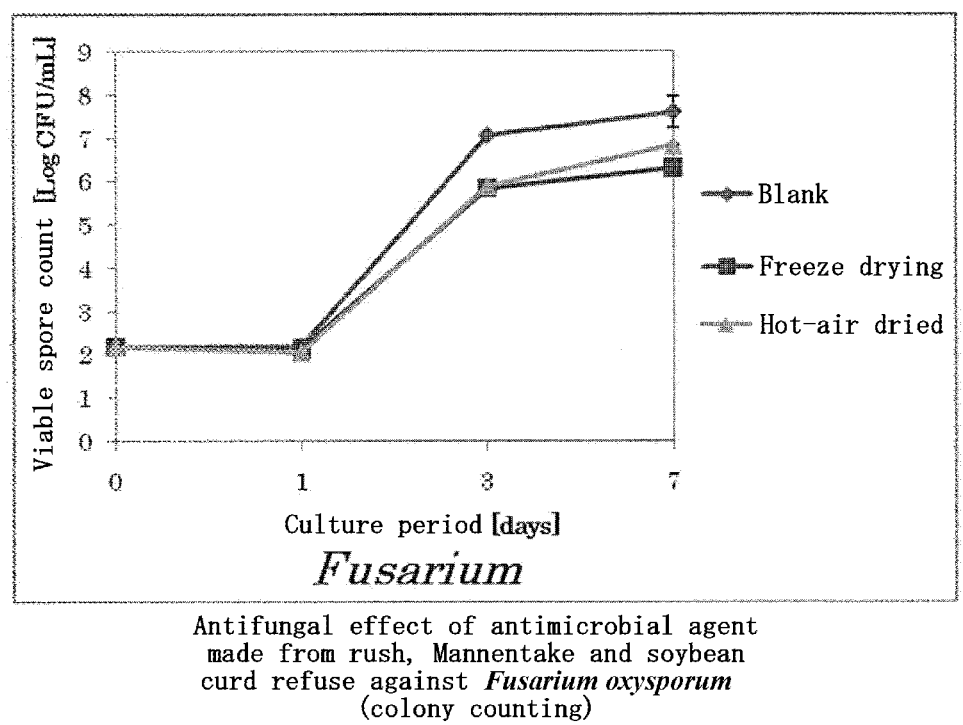
FIG. 1 shows the antifungal effect of the antimicrobial agent made from rush, Mannentake and okara (soybean curd refuse) against *Fusarium oxysporum* (colony counting), which agent is a practical product of the present invention, and is a graph showing comparison between blank, a freeze drying sample and a hot-air dried sample.

Hereinafter, embodiments of the antimicrobial agent and the method for producing the same relating to the present invention will be described, but the present invention is not limited to the embodiments.

The present embodiments use, as a plant belonging to the family Juncaceae which is one of raw materials, edible rush (usually cultivated without agricultural chemicals in a field and grown mainly using ground water). Rush itself has an antimicrobial activity. Rush is washed with water to remove attached substances and blanched, followed by cutting the blanched rush into a size with a length of 5 centimeters. In the blanching treatment, rush is blanched in hot water at 100° C. for 8 minutes (usually around 7 to 9 minutes). This treatment can inhibit discoloration and degeneration of rush and enables quality maintenance over a long period of time. In addition, since lye which is an unwanted component contained in rush is removed, cut rush in which only medical components are concentrated can be used.

Since Mannentake mycelium is used as mycelium, "okara (soybean curd refuse)" which makes a nutrient source for the mycelium is uniformly mixed with the cut rush by a mixing machine or by hand. This mixing is carried out for around 3 minutes.

After mixing, the mixture is sterilized by autoclaving at 121° C. for 60 to 90 minutes and cooled to room temperature. After cooling, Mannentake mycelium as a seed inoculum is inoculated to the mixture. At this time, mycelium is preferably inoculated under aseptic conditions (for example, inside a clean room).

Here, a method for culturing Mannentake mycelium as a seed inoculum is described in detail.

1) Using the tissue culture method, mycelium colonies are separated from a part of fruiting body of wild or naturally occurring Mannentake on potato dextrose agar (PDA) medium, thereby obtaining Mannentake mycelium.

2) The mycelium is cultured in a liquid medium or an agar medium.

2)-1 When culturing the mycelium in a liquid medium, in a 300-mL Erlenmeyer flask, around 100 mL of potato dextrose broth (PDB) medium is prepared and sterilized by autoclaving. After sterilization by autoclaving, Mannentake mycelium obtained in the above 1) is added to a suitable amount (10 mL in the present example) of sterilized water using a platinum loop and stirred. After that, the mycelium suspension is added to 1 to 2 mL of PDB medium and is cultured with shaking at 30° C. for 48 hours.

2)-2 Also when culturing the mycelium in an agar medium, in a 300-mL Erlenmeyer flask, around 100 mL of potato dextrose broth (PDB) medium is prepared and treated with autoclaving. On a PDA agar medium solidified after sterilization by autoclaving, Mannentake mycelium obtained in the above 1) is placed and cultured at 30° C. for 48 hours.

3) When using the culture prepared in 2)-1 as a seed inoculum, 20 mL of the seed inoculum 2)-1 is added to 200 g of rush and 200 g of okara (soybean curd refuse) and cultured.

4) When using the culture prepared in 2)-2 as a seed inoculum, the culture is cut off together with the agar medium by a spatula, added to 200 g of rush and 200 g of okara (soybean curd refuse) such that the mycelium amount is 10 g, and cultured.

The mixing ratio (the weight ratio) of each raw material may be changed as appropriate. In the present embodiments, 0.5 to 1.5 (1.0, here) of okara (soybean curd refuse) is mixed with 0.5 to 1.5 (1.0, here) of rush, the mixture is sterilized by autoclaving and then the seed inoculum is inoculated in an amount of 1 to 10% (for example, 10%) of the total amount. When represented in specific figures, as mentioned above, it is a form in that 20 mL (10 g) of the seed inoculum is inoculated to the mixture obtained by mixing 200 g of each of rush and okara (soybean curd refuse).

After Mannentake mycelium is thus inoculated to the mixture, a fermentation (culture) treatment was carried out under a condition of 20 to 30° C. considering a growth temperature for the mycelium. Although the fermentation period was around 1 to 3 months (one month, here), fermentation may be carried out for around 1 to 3 months or longer.

The crude material of the antimicrobial agent produced by the above production process was a) hot-air dried or b) freeze drying, thereby being able to produce a dried material of the antimicrobial agent. This antimicrobial agent is in the form of brownish granules.

a) Condition of hot-air drying: drying by hot air with the temperature of 60° C. for 12 hours.

b) Condition of freeze drying: drying using a vacuum freeze dryer. After the above-mentioned antimicrobial agent is placed into a freezer, the temperature inside the freezer is confirmed to be −30° C. under vacuum and the temperature inside the freezer is raised up to 30° C. Thus, after the temperature inside the freezer reaches 30° C., the agent is dried for 24 hours.

Subsequently, processes for producing antimicrobial agents depending on the intended purposes after the above-mentioned processes are described.

The uses thereof include A. an antiseptic agent for solid food, B. an agricultural chemical for plants, C. a therapeutic agent for athlete's foot, D. an antimicrobial agent for hands and fingers, E. an antimicrobial agent of bait for cultured fish, and the like.

In cases of A. an antiseptic agent for solid food, the above-mentioned dried material as it is or a finely-milled dried material (including a water extraction residue) is used by being sprayed on food or by being added to food.

In cases of B. an agricultural chemical for plants, the above-mentioned dried material is extracted with water and the extract is filtrated through a filter. The obtained filtrate is then concentrated, or sprayed onto soil and/or agricultural crops. At that time, addition of a spreading agent can reinforce the effect. Note a case where the water extraction residue is dried and then mixed with a soil conditioner or a fertilizer, and the mixture is applied to a plant rhizosphere. In that case, a synergistic effect of preventing the outbreak of pathogenic bacteria can be expected from both aspects of in and above the ground.

In cases of C. a therapeutic agent for athlete's foot and D. an antimicrobial agent for hands and fingers, the above-mentioned dried material is extracted with water and the extract is filtrated. The obtained filtrate is then concentrated, or sprayed or applied onto an affected area. Or, it may be further mixed with cream or other therapeutic agent for athlete's foot to facilitate application to an affected area. In addition, when being mixed with cream or the like, the above-mentioned dried material or a water extraction residue may be finely milled and used.

In cases of E. an antimicrobial agent of bait for cultured fish, the above-mentioned antimicrobial agent made from rush, Mannentake and okara (soybean curd refuse) before or after drying is used by being mixed with partial-dried solid bait (moist pellet) for cultured fish. When using the antimicrobial agent made from rush, Mannentake and okara (soybean curd refuse) before drying, it is mixed in an amount of 5 to 20% by weight of partial-dried solid bait for cultured fish. As a result, the bait becomes less perishable, which prevents environmental pollution caused by bait left uneaten in a sea area surrounding an aquaculture area and especially prevents the development of the red tide caused by eutrophication of the sea area The dried material is finely milled using a powdering machine conducting impact milling with a hammer fixed to a rotating disk rotating at high speed, until the average particle diameter becomes 20 μm or less.

In this example, water extraction of the dried material is carried out as follows. To 1000 mL of sterilized water, 0.0095 g of the dried material is added and extraction with shaking is carried out at a temperature of 25° C. at 70 rpm. After that, the solution is filtrated to obtain an extract. Or, 0.0095 g of the dried material is added to 1000 mL of sterilized water and is uniformly dispersed by ultrasonication at a temperature of 25° C., thereby obtaining an extract.

Although suitable embodiments of the present invention have been described as above, various additions, modifications or deletions are possible within a scope which does not depart from the spirit of the present invention. Especially, the plant belonging to the family Juncaceae may be at least one plant selected from Kohige, Hosoi, Inui (*Juncus yokoscensis*), Ezohosoi, Itoi (*Juncus maximowiczii* Buchen), Miyamai, Takanei, Hanabizekisho and Kusai (*Juncus tenuis*). In addition, the mycelium may be at least one Basidiomycete mycelium selected from Meshimakobu (*Fomes yucatensis*), Yamabushitake (*Hericium erinaceum*), Jew's ear mushroom (*Auricularia auricula-judae*), Tamogitake (*Pleurotus citrinopileatus*), Shiitake mushroom (*Lentinus edodes*) and Agaricus (Himematsutake) (*Agaricus subrufescens*).

Further, it is also possible to use wheat bran, rice bran, sake lees (shochu distillation residue) and soybean broth (cooking liquid of soy bean) as the nutrient source for the mycelium. Therefore, those are also included within the scope of the present invention.

It is also important to confirm an antimicrobial activity and a pharmacological activity of rush alone. However, as to the synergistic effect with Mannentake mycelium, tests concerning the physiological functions (antimicrobial effect and antioxidative activity) of "the antimicrobial agent made from rush and Mannentake (and okara (soybean curd refuse))" were carried out, so they will be described hereinafter.

Testing Methods

1. Evaluation of Antimicrobial Activity Against Mold 1-1: Powder of Rush, Mannentake and Okara (Soybean Curd Refuse)

As samples of the antimicrobial agent made from rush, Mannentake and okara (soybean curd refuse), there are two types of a freeze drying sample and a hot-air dried sample. These samples were placed into a crushing machine (produced by OSAKA CHEMICAL Co., Ltd.; model number WB-1) and milled at 25,000 rpm for 30 minutes to be finely milled.

1-2: Preparation of Sample-Added Medium

To 500 mL of sterilized water, 0.0095 g of a sample was added and then the sample was uniformly dispersed by ultrasonication. In a 300-mL Erlenmeyer flask, 2.4 g of potato dextrose broth medium (PDB medium) and 49 mL of ion-exchanged water were placed, 50 mL of the sample solution prepared as mentioned above was added therein, and the resulting solution was treated with autoclaving. Eventually, a PDB medium including the sample in a concentration of 9.5 μg/mL was prepared.

1-3: Test of Antifungal Activity

In the present tests, the following molds are used as assay strains and the evaluation of the antifungal activity of the samples was carried out.

Assay Strains

*Cladosporium cladosporioides* NBRC 30314

*Fusarium oxysporum* NBRC 31631

*Trichophyton violaceum* NBRC 31064

*Microsporum canis* NBRC 32464

To the sample liquid medium prepared in 1-2, 1 mL of the suspension of an assay strain was inoculated such that the initial concentration of the spore was $10^1$ to $10^2$ spores/mL, followed by shaking culture at a temperature of 30° C. at 70 rpm for 1 week. Here, one in which the bacterial suspension was inoculated to a PDB medium such that the initial concentration of the spore was $10^1$ to $10^2$ spores/mL was used as Blank. Sampling was carried out on days 1, 3 and 7 of culture, and cultivation was carried out at 30° C. using potato dextrose agar medium (PDA medium) as an enrichment medium. The experimental results were determined on a scale of 6 using an evaluation method by visual observation shown in Table. 1.

Along with this visual evaluation, colony counting was used in order to calculate the number of spores remaining with time.

TABLE 1

Standard growth scores

| Score | Observed growth |
|---|---|
| 1 | Spores abundantly formed |
| 2 | Spores lightly formed |
| 3 | Spores slightly formed |
| 4 | Pich growth of hypha (complete coverage) |
| 5 | Slight growth of hypha |
| 6 | No growth |

2. Evaluation of Antimicrobial Activity Against Bacteria
2-1: Powder of Rush, Mannentake and Okara (Soybean Curd Refuse)

As samples of the antimicrobial agent made from rush, Mannentake and okara (soybean curd refuse), there are two types of a freeze drying sample and a hot-air dried sample. These samples were placed into a crushing machine (produced by OSAKA CHEMICAL Co., Ltd.; model number WB-1) and milled at 25,000 rpm for 30 min to be finely milled.

2-2: Preparation of Sample-Added Medium

To 500 mL of sterilized water, 0.0095 g of a sample was added and the sample was uniformly dispersed by ultrasonication. In a 300-mL Erlenmeyer flask, 0.8 g of nutrient broth medium (NB medium) and 49 mL of ion-exchanged water were placed, 50 mL of the sample solution prepared as mentioned above was added therein, and the resulting solution was treated with autoclaving. Eventually, an NB medium including the sample in a concentration of 9.5 µg/mL was prepared.

2-3: Test of Antimicrobial Activity

In the present experiments, the following bacteria are used as assay strains and the evaluation of the antimicrobial activity of the samples was carried out.

Assay Strains
  Bacillus subtilis IFO 3335
  Micrococcus luteus IFO 3333
  Escherichia coli IFO 3972
  Staphylococcus aureus IFO 12732

To the sample liquid medium prepared in 2-2, 1 mL of the suspension of an assay strain was inoculated such that the initial concentration of the bacteria number was $10^1$ to $10^2$ CFU/mL, followed by shaking culture at 30° C. at 70 rpm for 3 days. Here, one in which the bacterial suspension was inoculated to an NB medium such that the initial concentration of the bacteria number was $10^1$ to $10^2$ CFU/mL was used as Blank. Sampling was carried out on days 1, 2 and 3 of culture, and cultivation was carried out at 30° C. using nutrient agar medium (NA medium) as an enrichment medium. The number of viable bacteria remaining was calculated with time by colony counting.

3. Measurement of Antioxidative Activity

In the measurement of antioxidative activity, β-carotene (100 mg/100 mL chloroform), linoleic acid (4 g/100 mL chloroform) and a Tween 80 solution (4 g/100 mL chloroform) were prepared, and 0.55 mL, 0.55 mL and 1.1 mL of each were placed in a 200-mL Erlenmeyer flask. To the mixture, 110 mL of distilled water was added to dissolve the contents, thereby preparing a linoleic acid and β-carotene solution. To 90 mL of this solution, 8 mL of a 0.2 M phosphate buffer solution (pH 6.8) was added and the mixture was stirred gently. Then, 4.9 mL of the mixture was placed in a test tube, 0.1 mL of the sample (an extract of the sample of rush, Mannentake and okara (soybean curd refuse)) was added thereto and mixed therewith, and the resulting mixture was rapidly transferred to a reaction vessel at 50° C. and the decreased amount of absorbance (470 nm) was determined from 15 minutes to 45 minutes after the addition of the sample. Further, the decreased amount determined was divided by the decreased amount of absorbance of the reaction solution prepared by adding a BHA solution (a 2:8 (v/v) mixed solution of 1 mg/100 mL of 0.1 M acetic acid buffer (pH 4.5) and methanol) as a reference solution to determine the antioxidative activity value.

Test Results
1. Test Results of Antifungal Activity
1-1 Phytopathogenic Fungus (*Fusarium* Sp.)

*Fusarium* sp. belongs to imperfect fungi. *Fusarium* sp. lives in soil and withers plants (mainly root parts) as a phytopathogenic fungus, which often causes problems. In addition, since *Fusarium* sp. can grow even under low-humidity and cold conditions, it is very difficult to control. It is also known that *Fusarium* sp. produces a low temperature toxin (mycotoxin), which causes poisoning symptoms (nausea, emesis, abdominal pain, diarrhea, hematopoietic disorder, immunodeficiency and the like) when entering the body. Crescent-shaped conidia are produced and the color of the spores is originally white. It gradually turns red as days go by and finally deep red colonies are formed. Accordingly, in the present study, tests were carried out regarding the antifungal effect of "the antimicrobial agent made from rush, Mannentake and okara (soybean curd refuse)" against *Fusarium oxysporum*.

Figure 2:
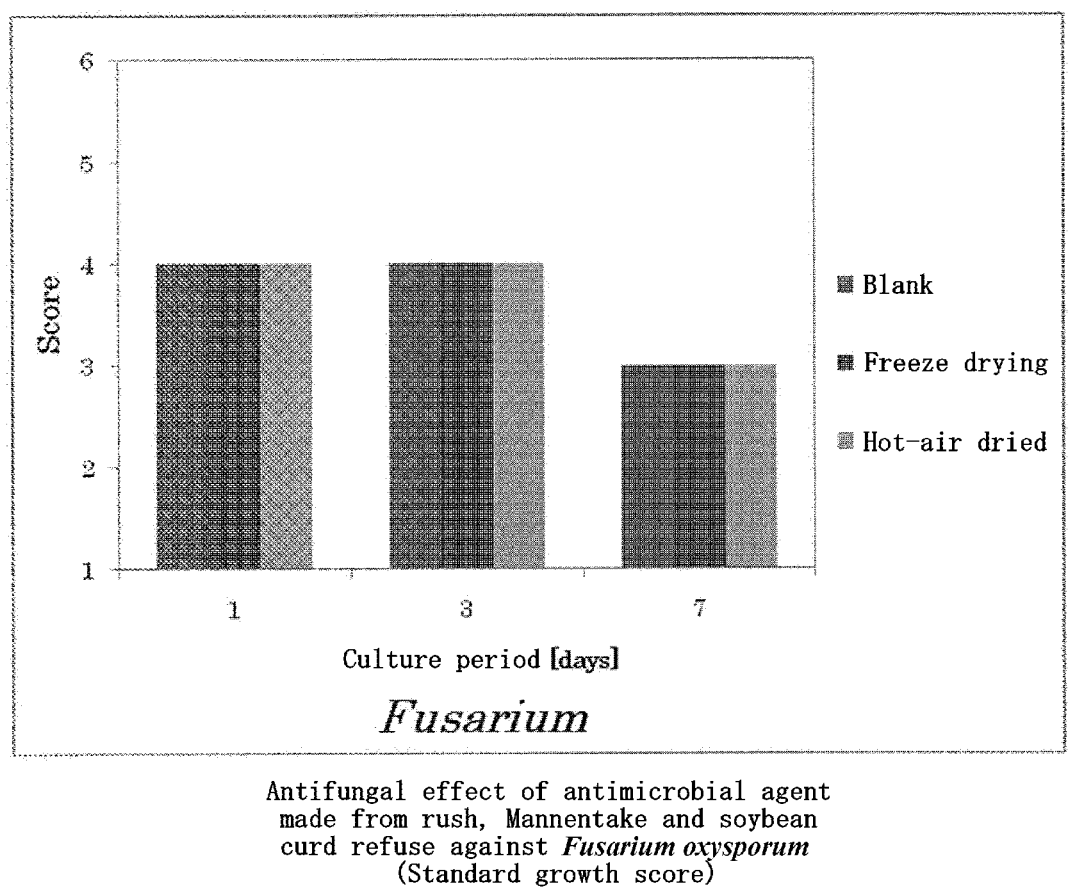
FIG. 2 shows the antifungal effect of the antimicrobial agent made from rush, Mannentake and okara (soybean curd refuse) against *Fusarium oxysporum* (Standard growth score), which agent is a practical product of the present invention, and is a graph showing comparison between blank, a freeze drying sample and a hot-air dried sample.

The results are shown in FIG. 1 (colony counting) and FIG. 2 (Standard growth score) in the accompanying drawings. The results of colony counting indicate that the present antimicrobial agent exerted the antifungal effect against *Fusarium oxysporum* in the order of 1 to 2. Between the hot-air dried sample and the freeze drying sample, although the freeze drying sample exerted a little higher antifungal effect, no big difference was observed. However, a clear difference from blank was not observed in Standard growth score.

The concentration of the extract is 9.5 µg/mL (0.0095 mg/mL), so the antifungal effect was exerted in the low concentration of 0.95%, mathematically. From the fact that *Fusarium oxysporum* can be controlled in the order of 1 to 2 with such a low concentration, the applicability of the extract as an agricultural chemical can be referred to. *Fusarium* sp. is known as a pathogenic fungus of a wide variety of plants such as tomato, banana, sweet potato and plants belonging to the family Fabaceae, Cucurbitaceae and Brassicaceae. It is a significant result that "the antimicrobial agent made from rush, Mannentake and okara (soybean curd refuse)" has the antifungal effect against *Fusarium* sp., and the range of applicability of the extract as an agricultural chemical will be broadened from now on.

1-2 Indoor Pollution Mold (*Cladosporium* Sp.)

*Cladosporium* sp. belongs to imperfect fungi. *Cladosporium* sp. is also the most common mold among mold suspended in the air. *Cladosporium* sp. is found not only in tatami (straw mat), but also in everywhere inside a house such as a bathroom, futon (Japanese mattress), a restroom, a lavatory and a kitchen. Other than inside a house, *Cladosporium* sp. also grows on various foods such as manju (Japanese bun stuffed with sweetened bean paste), cakes and vegetables. *Cladosporium* sp. forms colonies of dark green to black in color. *Cladosporium* sp. itself does not produce toxic substances, but is of a problem as an allergen for asthma or the like. Accordingly, in the present study, tests were carried out regarding the antifungal effect of "the antimicrobial agent made from rush, Mannentake and okara (soybean curd refuse)" against *Cladosporium cladosporioides*.

Figure 3:
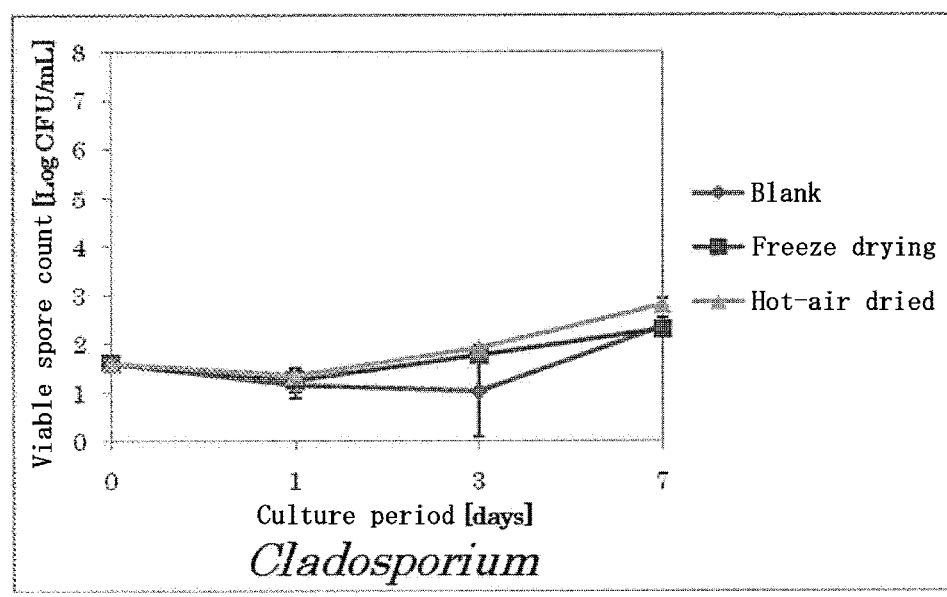
FIG. 3 shows the antifungal effect of the antimicrobial agent made from rush, Mannentake and okara (soybean curd refuse) against *Cladosporium cladosporioides* (colony counting), which agent is a practical product of the present invention, and is a graph showing comparison between blank, a freeze drying sample and a hot-air dried sample.
Figure 4:
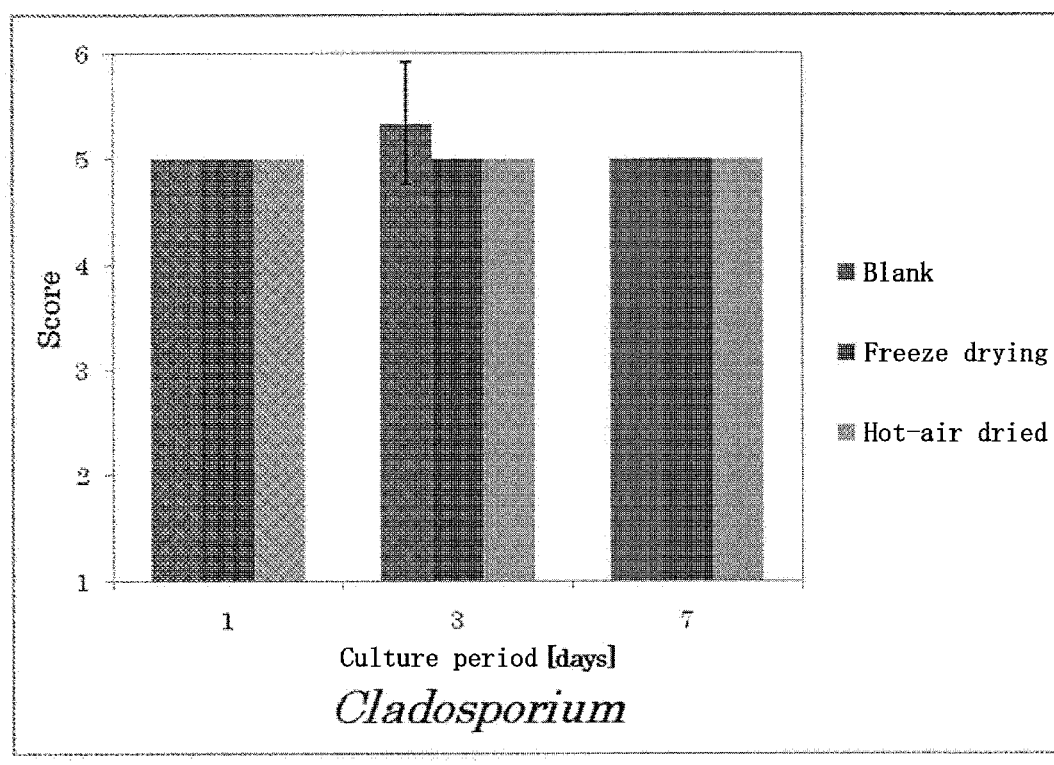
FIG. 4 shows the antifungal effect of the antimicrobial agent made from rush, Mannentake and okara (soybean curd refuse) against *Cladosporium cladosporioides* (Standard growth score), which agent is a practical product of the present invention, and is a graph showing comparison between blank, a freeze drying sample and a hot-air dried sample.

The results are shown in FIG. 3 (colony counting) and FIG. 4 (Standard growth score) in the accompanying drawings. In all cases, the extracts did not have the antifungal effect against *Cladosporium cladosporiaides*.

1-3 Athlete's Foot Pathogenic Mold (Trichophytosis Molds)

Athlete's foot is one kind of trichophytosis. Trichophytosis is dermatomycosis caused by cutaneous infection by a kind of mold called Trichophytosis molds. Trichophytosis molds include *Trichophyton* sp. and *Microsporum* sp., and prefers a hot and humid environment. Trichophytosis molds infects various parts of the human body and one-fourth of all Japanese are said to suffer from trichophytosis. The majority of infection are thought to be familial infection, and routine prevention of trichophytosis is very important. Accordingly, in the present study, tests were carried out regarding the antifungal effect of "the antimicrobial agent made from rush, Mannentake and okara (soybean curd refuse)" against *Trichophyton violaceum* and *Microsporum canis*.

Figure 5:
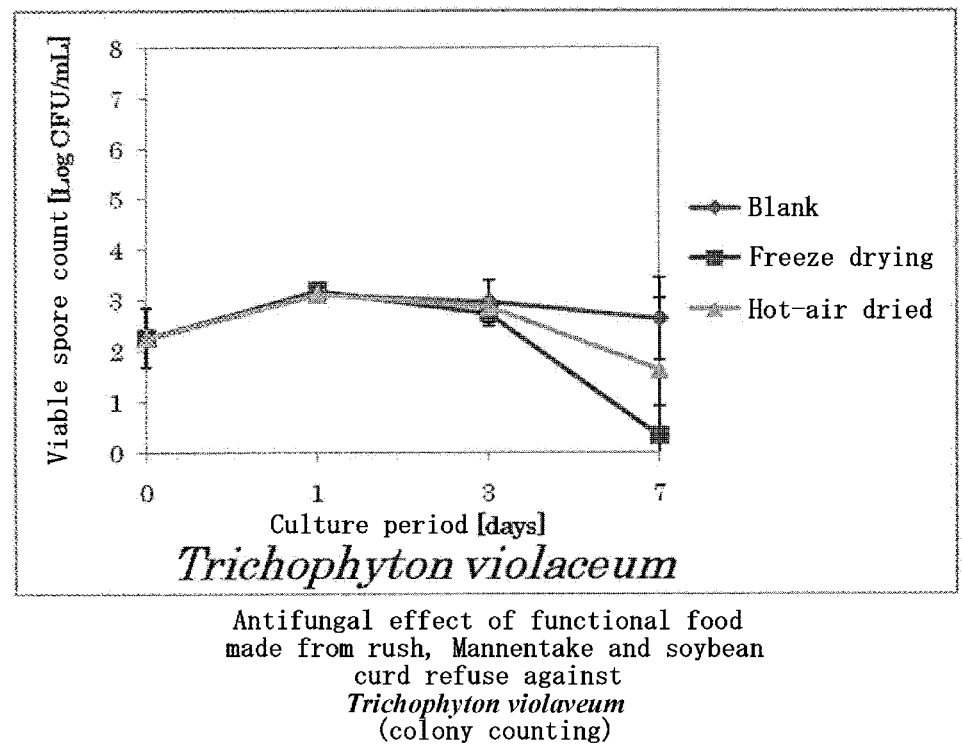
FIG. 5 shows the antifungal effect of the antimicrobial agent made from rush, Mannentake and okara (soybean curd refuse) against *Trichophyton violaeum* (colony counting), which agent is a practical product of the present invention, and is a graph showing comparison between blank, a freeze drying sample and a hot-air dried sample.
Figure 6:
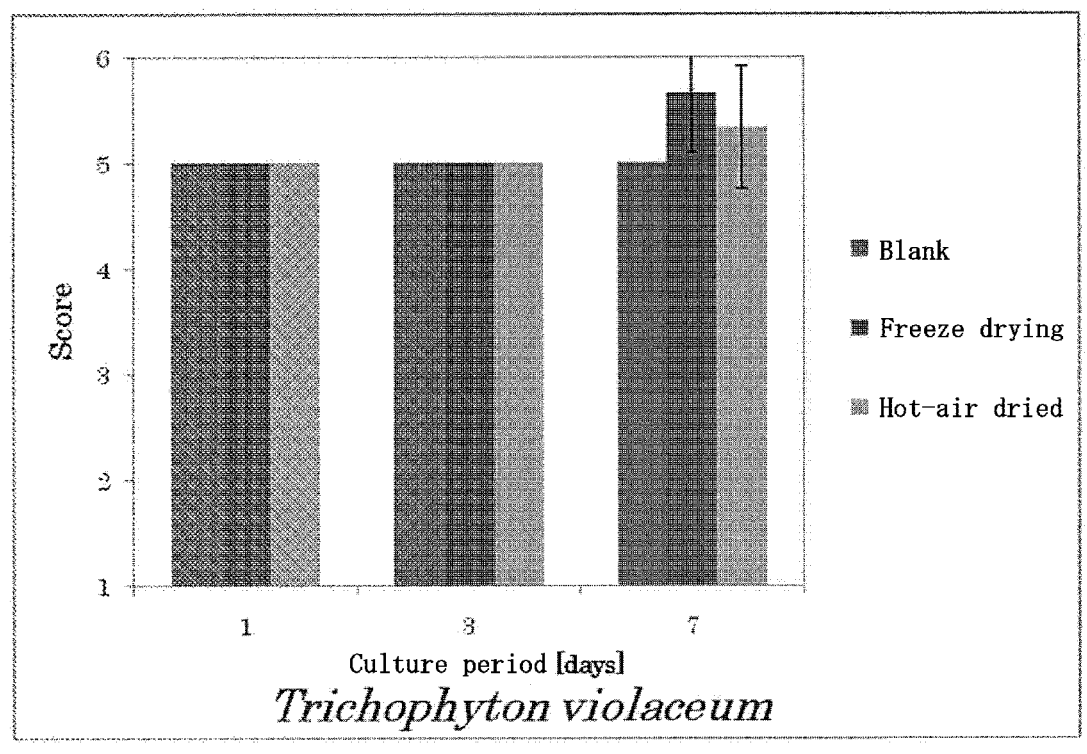
FIG. 6 shows the antifungal effect of the antimicrobial agent made from rush, Mannentake and okara (soybean curd refuse) against *Trichophyton violaeum* (Standard growth score), which agent is a practical product of the present invention, and is a graph showing comparison between blank, a freeze drying sample and a hot-air dried sample.
Figure 7:
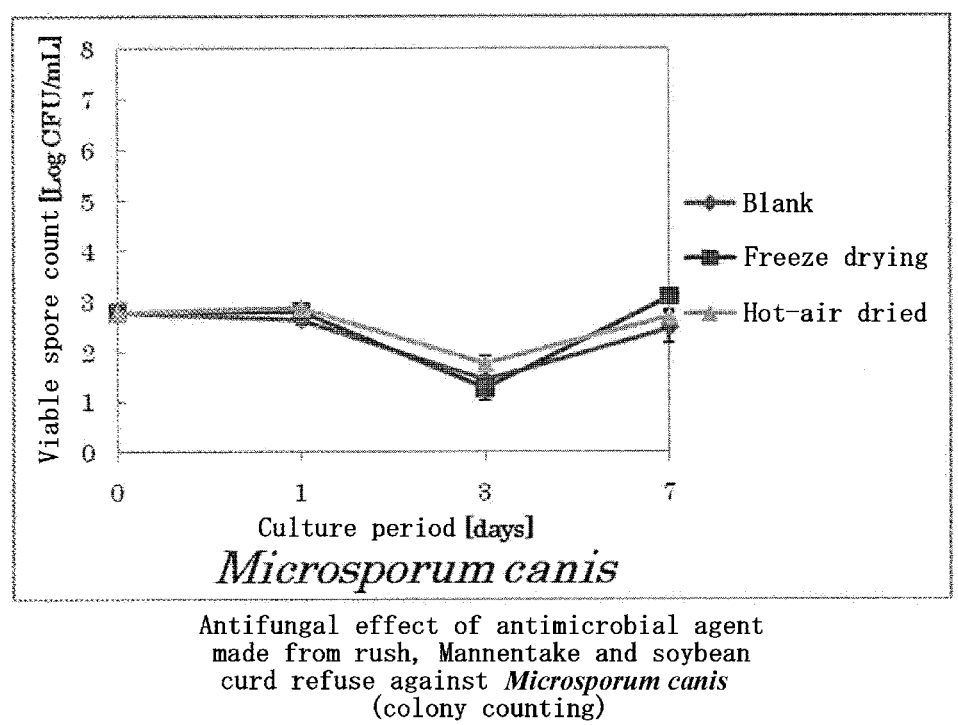
FIG. 7 shows the antifungal effect of the antimicrobial agent made from rush, Mannentake and okara (soybean curd refuse) against *Microsporum canis* (colony counting), which agent is a practical product of the present invention, and is a graph showing comparison between blank, a freeze drying sample and a hot-air dried sample.
Figure 8:
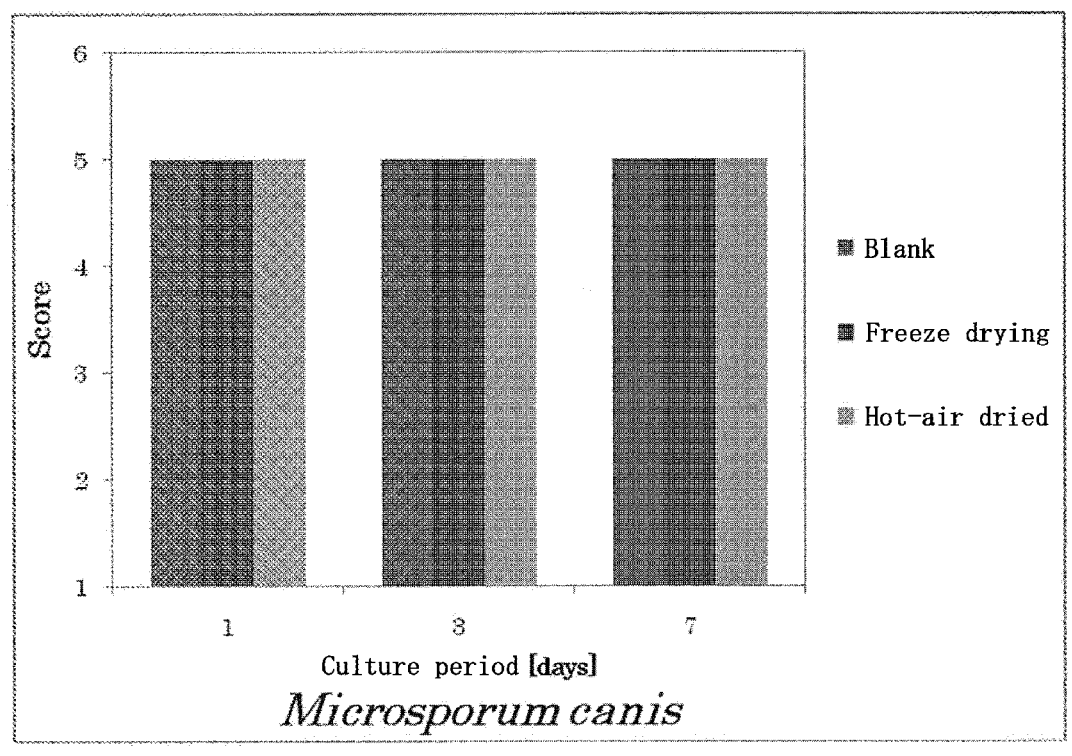
FIG. 8 shows the antifungal effect of the antimicrobial agent made from rush, Mannentake and okara (soybean curd refuse) against *Microsporum canis* (Standard growth score), which agent is a practical product of the present invention, and is a graph showing comparison between blank, a freeze drying sample and a hot-air dried sample.

The results for *Trichophyton violaceum* are shown in FIG. 5 (colony counting) and FIG. 6 (Standard growth score) in the accompanying drawings and the results for *Microsporum canis* are shown in FIG. 7 (colony counting) and FIG. 8 (Standard growth score) in the accompanying drawings. The results indicate that although a high antifungal effect against *Trichophyton violaceum* was not observed until day 3 of culture, a clear antifungal effect was observed in the sample cultured for 7 days. Especially, *Trichophyton violaceum* was almost completely killed in the freeze drying sample according to the results.

In the Standard growth score of *Trichophyton violaceum*, a clear difference was not observed compared with blank, so grown *Trichophyton violaceum* was killed when cultured for 7 days. That is, the antimicrobial agent made from rush, Mannentake and okara (soybean curd refuse) showed a delayed effect against *Trichophyton violaceum*, which was a very interesting result. On the other hand, the antifungal effect against *Microsporum canis* was not observed.

*Trichophyton* sp. is a pathogenic fungus which is the most common cause of trichophytosis. In addition, since *Microsporum* sp. prefers to parasitize in dogs and cats, it infects humans via pets. Therefore, the obtained antifungal effect against *Trichophyton* sp. widely broadens the possibility as a therapeutic agent for athlete's foot as a result.

Incidentally, rush has an antifungal effect against *Trichophyton violaceum* by itself. If used solely, rush exerts the effect only when the concentration is 5% or more. The concentration of the extract is 9.5 µg/mL (0.0095 mg/mL), so the antifungal effect was exerted in the low concentration of 0.95%, mathematically. It can be said that this result is a useful data showing that the synergistic effect by the antimicrobial agent made from rush, Mannentake and okara (soybean curd refuse) strengthened the antifungal activity compared with that of rush alone.

2. Test Results of Antimicrobial Activity 2-1 Bacteria as Hygiene Indicator (*Escherichia coli*)

*Escherichia coli* is a Gram-negative *bacillus*, belongs to facultative anaerobe and is one of major species among bacteria existing in environment. This bacterium is also an enteric bacterium and exists in digestive tracts, especially in the large intestine, of warm-blooded animals (birds and mammals). *Escherichia coli* is one of the model organisms as a representative bacterium and not only used as a material for various studies, but also utilized for production of useful chemical substances by incorporating genes therein. There exist nonpathogenic and pathogenic *Escherichia coli*, and nonpathogenic *Escherichia coli* is harmless to the human body. However, pathogenic *Escherichia coli* becomes a cause of diseases in some cases. In the human body, *Escherichia coli* serves as a pathogen when invading blood and the urinary system. As *Escherichia coli* produces endotoxins, sepsis by *Escherichia coli* causes severe endotoxic shock. The most frequent cause of sepsis (in cases where the cause is clarified) is urinary tract infection and *Escherichia coli* is the most common bacterium causing urinary tract infection.

Figure 9:
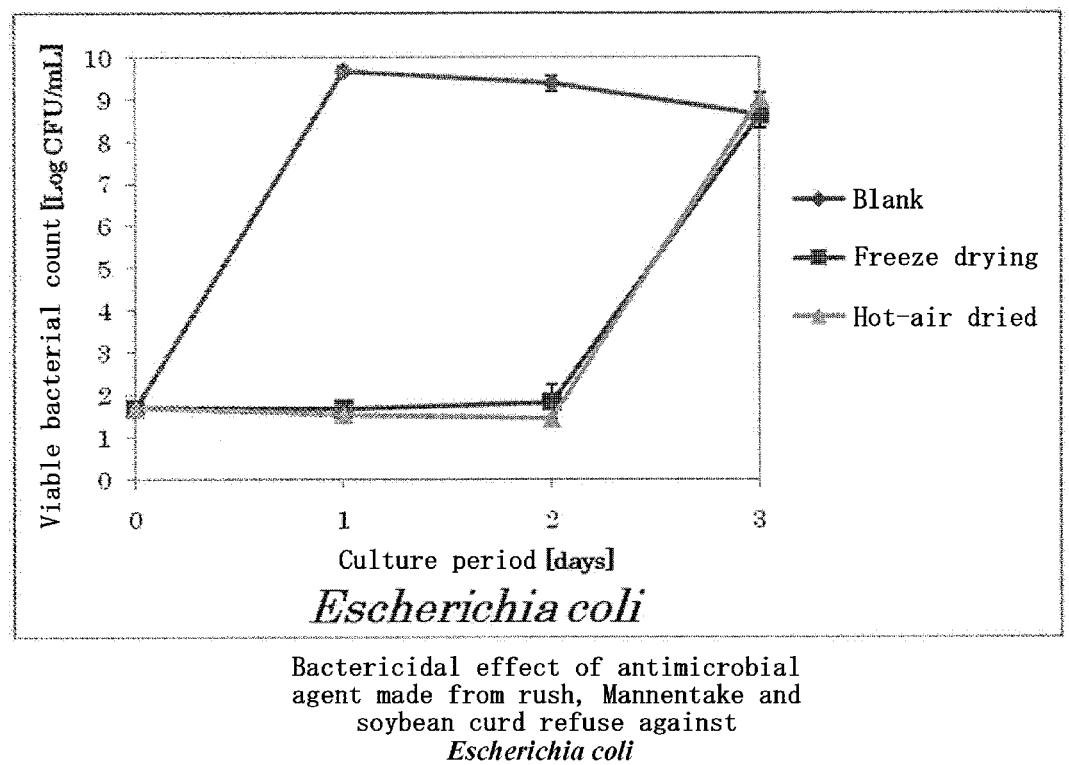
FIG. 9 shows the antimicrobial effect of the antimicrobial agent made from rush, Mannentake and okara (soybean curd refuse) against *Escherichia coli*, which agent is a practical product of the present invention, and is a graph showing comparison between blank, a freeze drying sample and a hot-air dried sample.

Accordingly, in the present study, investigations were carried out regarding the antimicrobial effect of "the antimicrobial agent made from rush, Mannentake and okara (soybean curd refuse)" against *Escherichia coli*. The results are shown in FIG. 9.

The results indicate that a high antimicrobial effect in the order of around 7 or more compared with blank was observed both in the freeze drying sample and the hot-air dried sample until day 2 of culture. However, no significant difference was observed compared with blank on day 3 of culture. Therefore, it was revealed that the effect is a bacteriostatic effect.

2-2 Putrefactive Bacterium (*Bacillus* Sp.)

Figure 10:
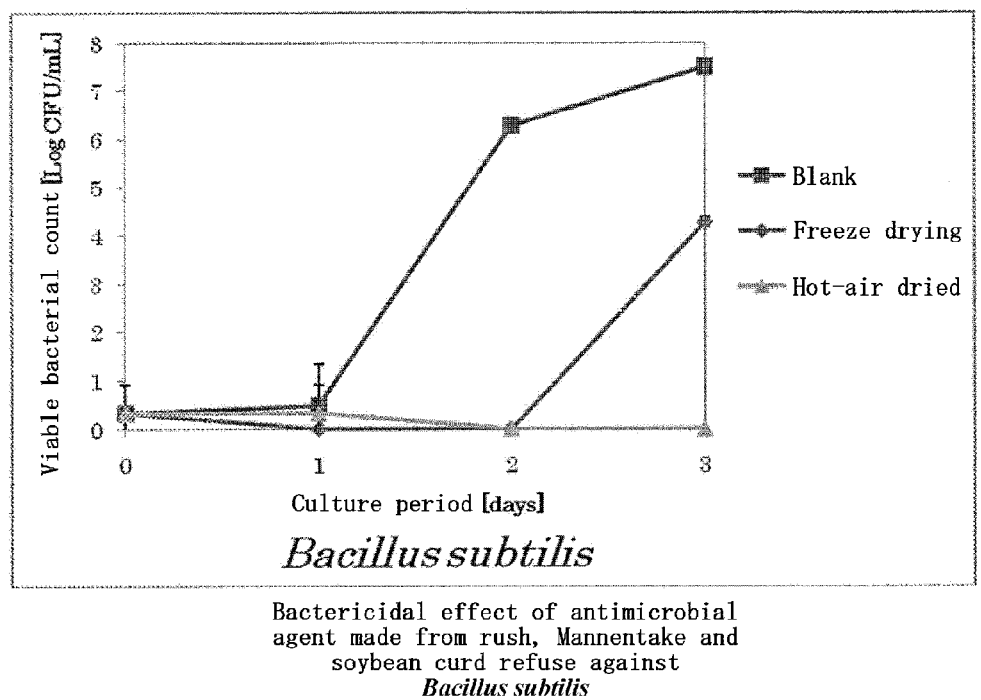
FIG. 10 shows the antimicrobial effect of the antimicrobial agent made from rush, Mannentake and okara (soybean curd refuse) against *Bacillus subtilis*, which agent is a practical product of the present invention, and is a graph showing comparison between blank, a freeze drying sample and a hot-air dried sample.

*Bacillus* sp. is one kind of eubacteria occurring ubiquitously in nature. Due to its strong degradation ability of organic substances, *Bacillus* sp. is known as a putrefactive bacterium. Accordingly, in the present study, tests were carried out regarding the antimicrobial effect of "the antimicrobial agent made from rush, Mannentake and okara (soybean curd refuse)" against *Bacillus subtilis*. The results are shown in FIG. 10 in the accompanying drawings.

The results indicate that a high antimicrobial effect in the order of around 6 or more compared with blank was observed both in the freeze drying sample and the hot-air dried sample on day 2 of culture. In the samples on day 3 of culture, no bacteria were detected in the hot-air dried sample (the antimicrobial effect in the order of around 7). Although a high antimicrobial effect (the antimicrobial effect in the order of around 3) was observed in the freeze drying sample compared with blank, bacteria were detected in the order of around 4 compared with the hot-air dried one. Here, it was again revealed that the effect is a bacteriostatic effect.

2-3 Human Indigenous Bacteria (*Staphylococcus* Sp., *Micrococcus* Sp.)

*Staphylococcus aureus* is one of *Staphylococcus* sp. which is an indigenous bacterium in skin and digestive tracts (intestines) (enteric bacterium) of humans and animals. It is also a bacterium causing various epidermal infections such as human abscess, food poisoning, and also potentially lethal infectious diseases such as pneumonia, meningitis and sepsis. *Micrococcus* sp. is one genus of eubacteria classified as Gram-positive bacteria and is included in *Actinomyces* taxonomically. It is a bacterium normally present in human and includes many bacterial strains causing food decomposition. *Micrococcus* sp. does not have an ability of forming mycelia and is widely distributed in soils and various water systems.

Figure 11:
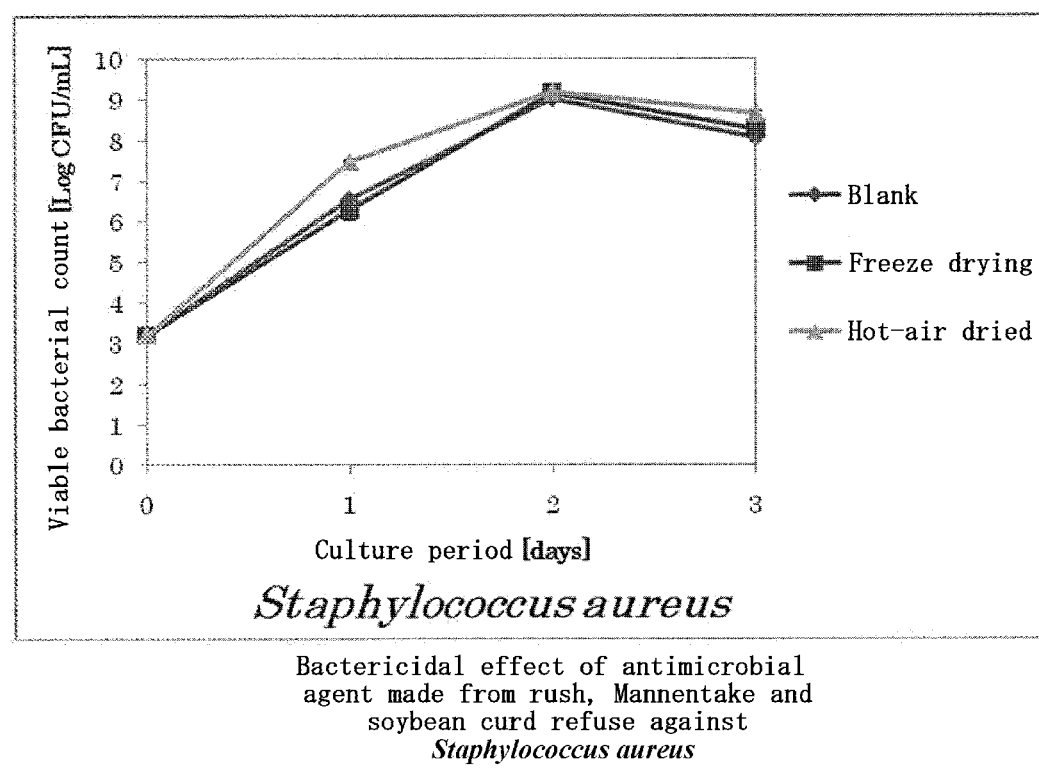
FIG. 11 shows the antimicrobial effect of the antimicrobial agent made from rush, Mannentake and okara (soybean curd refuse) against *Staphylococcus aureus*, which agent is a practical product of the present invention, and is a graph showing comparison between blank, a freeze drying sample and a hot-air dried sample.

Accordingly, in the present study, tests were carried out regarding the antimicrobial effect of "the antimicrobial agent made from rush, Mannentake and okara (soybean curd refuse)" against *Staphylococcus aureus* and *Micrococcus luteus*. The results are shown in FIG. 11 (*Staphylococcus aureus*) and FIG. 12 (*Micrococcus luteus*) in the accompanying drawings.

The results indicate that the antimicrobial effect was not observed in all cases.

2-4 Antimicrobial Effect of Rush Alone

The antibacterial spectrum of the water extract of rush is shown in Table 2. Rush exhibited the antimicrobial activity in the ranges of 0.78 to 100 mg/mL of MIC values against food poisoning bacteria including *Salmonella* sp., *Staphylococcus* sp., EHEC O157, O26 and O111, putrefactive bacteria such as *Bacillus* sp. and *Micrococcus* sp., and further *Legionella pneumophila* which is a bacterium causing Legionnaires' disease. The strongest antimicrobial activity was exhibited against *Escherichia coli* and the MIC value was 0.78 mg/mL. The concentration of the extract was 9.5 μg/mL (0.0095 mg/mL), so the antimicrobial agent made from rush, Mannentake and okara (soybean curd refuse) exerted the antimicrobial effect against *Escherichia coli* and *Bacillus subtilis* at a very low concentration, mathematically.

TABLE 2

Antimicrobial spectrum of rush

| Assay strain | MIC (mg/ml) |
| --- | --- |
| *Bacillus subtilis* IFO 3335 | 1.6 |
| *Salmonella typhimurium* IFO 13245 | 3.1 |
| *Micrococcus luteus* IFO 3333 | 1.6 |
| *Escherichia coli* IFO 3972 | 0.78 |
| *Staphylococcus aureus* IFO 12732 | 50 |
| *Pseudomonas Fluorescens* IFO 3507 | — |
| *Saccharomyces cerevisiae* IFO 2363 | — |
| *Aspergillus oryzae* IFO 30102 | — |
| *Rhizopus japonicus* IFO 4697 | — |
| EHEC O157: H7 (VT1) | 100 |
| EHEC O157: H7 (VT2) | 100 |
| EHEC O157: H7 (VT1/VT2) | 100 |
| EHEC O26: H11 (VT1) | 100 |
| EHEC O111: H8 (VT1) | 100 |
| *Bifidobacterium bifidum* IFO 14252 | — |
| *Enterococcus faecalis* IFO 3971 | — |
| *Enterococcus faecalis* IFO 12580 | — |
| *Enterococcus faecium* IFO 3128 | — |
| *Streptococcus bovis* IFO 12057 | — |
| *Bacteroides vulgatus* IFO 14291 | — |
| *Legionella pneumophila* SGI | 20 |

(—: not detected)

3. Test of Antioxidative Activity

In this study, evaluation was carried out regarding the antioxidant tests of the antimicrobial agent made from rush, Mannentake and okara (soybean curd refuse). Unfortunately, however, an antioxidative activity was not detected.

DRAWINGS

FIG. 1
1 Viable spore count
2 Culture period
3 Freeze drying
4 Antifungal effect of antimicrobial agent made from rush, Mannentake and okara (soybean curd refuse) against *Fusarium oxysporum* (colony counting)

FIG. 2
1 Freeze drying Hot-air dried
2 Culture period
3 Antifungal effect of antimicrobial agent made from rush, Mannentake and okara (soybean curd refuse) against *Fusarium oxysporum* (Standard growth score)

FIG. 3
1 Viable spore count
2 Culture period
3 Freeze drying Hot-air dried
4 Antifungal effect of antimicrobial agent made from rush, Mannentake and okara (soybean curd refuse) against *Cladosporium cladosporioides* (colony counting)

FIG. 4
1 Culture period
2 Freeze drying Hot-air dried
3 Antifungal effect of antimicrobial agent made from rush, Mannentake and okara (soybean curd refuse) against *Cladosporium cladosporioides* (Standard growth score)

FIG. 5
1 Viable spore count
2 Culture period
3 Freeze drying Hot-air dried
4 Antifungal effect of functional food made from rush, Mannentake and okara (soybean curd refuse) against *Trichophyton violaveum* (colony counting)

FIG. 6
1 Culture period
2 Freeze drying Hot-air dried
3 Antifungal effect of antimicrobial agent made from rush, Mannentake and okara (soybean curd refuse) against *Trichophyton violaveum* (Standard growth score)

FIG. 7
1 Viable spore count
2 Culture period
3 Freeze drying Hot-air dried
4 Antifungal effect of antimicrobial agent made from rush, Mannentake and okara (soybean curd refuse) against *Microsporum canis* (colony counting)

FIG. 8
1 Culture period
2 Freeze drying Hot-air dried
3 Antifungal effect of antimicrobial agent made from rush, Mannentake and okara (soybean curd refuse) against *Microsporum canis* (Standard growth score)

FIG. 9
1 Viable bacterial count
2 Culture period
3 Freeze drying Hot-air dried
4 Antimicrobial effect of antimicrobial agent made from rush, Mannentake and okara (soybean curd refuse) against *Escherichia coli*

FIG. 10
1 Viable bacterial count
2 Culture period
3 Freeze drying Hot-air dried
4 Antimicrobial effect of antimicrobial agent made from rush, Mannentake and okara (soybean curd refuse) against *Bacillus subtilis*

FIG. 11
1 Viable bacterial count
2 Culture period
3 Freeze drying Hot-air dried
4 Antimicrobial effect of antimicrobial agent made from rush, Mannentake and okara (soybean curd refuse) against *Staphylococcus aureus*

Figure 12:
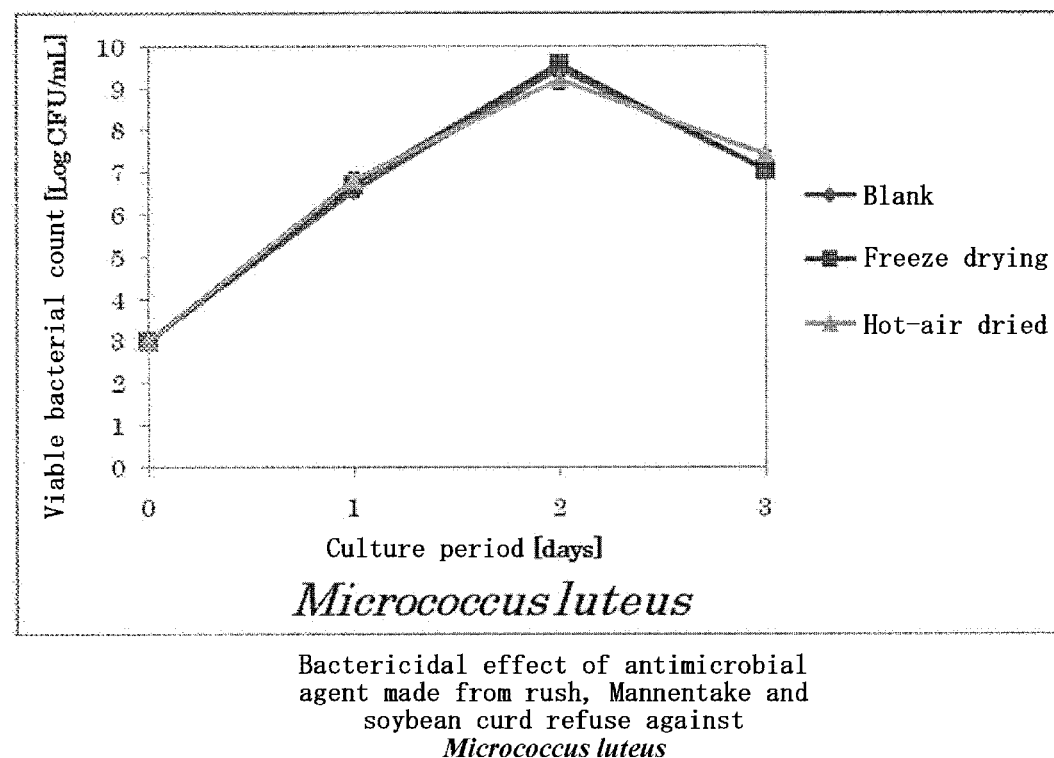
FIG. 12 shows the antimicrobial effect of the antimicrobial agent made from rush, Mannentake and okara (soybean curd refuse) against *Micrococcus luteus*, which agent is a practical product of the present invention, and is a graph showing comparison between blank, a freeze drying sample and a hot-air dried sample.

FIG. 12
1 Viable bacterial count
2 Culture period
3 Freeze drying Hot-air dried
4 Antimicrobial effect of antimicrobial agent made from rush, Mannentake and okara (soybean curd refuse) against *Micrococcus luteus*

The invention claimed is:
1. A method for producing an antimicrobial agent, comprising cutting, or cutting and then milling a plant belonging to the family Juncaceae: mixing the cut or cut and milled plant with a nutrient source for a seed culture of mushroom mycelia, to form a mixture; inoculating the seed culture of mycelia is inoculated to the mixture of the plant belonging to the family Juncaceae and the nutrient source and then culturing the seed culture at a temperature suitable for the growth of the seed culture of mycelia to produce a culture containing the antimicrobial agent.

2. The method for producing an antimicrobial agent according to claim 1, wherein the plant belonging to the family Juncaceae is at least one plant selected from the group consisting of rush (*Juncus decipiens, Juncus yokoscensis, Juncus maximowiczii,* and *Juncus tenuis.*

3. The method for producing an antimicrobial agent according to claim 1, wherein the seed culture of mycelia is at least one Basidiomycete mycelium selected from the group consisting of Mannentake/Reishi (*Ganoderma lucidum*), Meshimakobu (*Fomes yucatensis*), Yamabushitake (*Hericium erinaceum*), Jew's ear mushroom (*Auricularia auricula-judae*), Benikusunokitake (shoshi) (*Antrodia camphorate*), Shiitake mushroom (*Lentinus edodes*) and *Agaricus* (Himematsutake) (*Agaricus subrufescens*).

4. The method for producing an antimicrobial agent according to claim 1, wherein the nutrient source is at least one selected from okara, wheat bran, rice bran, sake lees and soybean broth.

5. The method for producing an antimicrobial agent according to claim 1, wherein the plant belonging to the family Juncaceae is rush, the seed culture of mushroom mycelia is Mannentake mycelium, and the nutrient source is okara (soybean curd refuse).

6. A method for producing an antimicrobial agent, wherein, in the method for producing an antimicrobial agent according to claim 5, the mixture is sterilized by autoclaving at 121° C. for 60 to 90 minutes and cooled, and then the seed culture of mycelia is inoculated to the mixture and cultured at a temperature of 20 to 30° C. for 1 to 3 months or longer.

7. A method for producing an antimicrobial agent, wherein, in the method for producing an antimicrobial agent according to claim 5, the mixing ratio (the weight ratio) of the mixture is 0.5 to 1.5 of okara (soybean curd refuse) to 0.5 to 1.5 of rush, the mixture is sterilized by autoclaving, and then Mannentake mycelium is inoculated in an amount of 1 to 10% of the total weight of the mixture.

8. A water-soluble extract of the antimicrobial agent obtained by drying the culture containing the antimicrobial agent produced by the method of claim 5, and extracting the dried material with water to produce the extract.

9. A powdered antimicrobial agent produced by drying and then milling the culture containing the antimicrobial agent produced by the method according to claim 5.

10. A powdered antimicrobial agent prepared by drying the culture containing the antimicrobial agent produced by the method of claim 5 to form a dried material: extracting the dried material with water and drying the extract to form a dried material residue; and milling the dried material residue.

11. The method for producing an antimicrobial agent according to claim 2, wherein the seed culture of mycelia is at least one Basidiomycete mycelium selected from the group consisting of Mannentake/Reishi (*Ganoderma lucidum*), Meshimakobu (*Fomes yucatensis*), Yamabushitake (*Hericium erinaceum*), Jew's ear mushroom (*Auricularia auricula-judae*), Benikusunokitake (shoshi) (*Antrodia camphorate*), Shiitake mushroom (*Lentinus edodes*) and *Agaricus* (Himematsutake) (*Agaricus subrufescens*).

12. The method for producing an antimicrobial agent according to claim 2, wherein the nutrient source is at least one selected from okara, wheat bran, rice bran, sake lees and soybean broth.

13. The method for producing an antimicrobial agent according to claim 3, wherein the nutrient source is at least one selected from okara, wheat bran, rice bran, sake lees and soybean broth.

14. The method for producing an antimicrobial agent according to claim 2, wherein the plant belonging to the family Juncaceae is rush, the seed culture of mushroom mycelia is Mannentake mycelium, and the nutrient source is okara (soybean curd refuse).

15. The method for producing an antimicrobial agent according to claim 3, wherein the plant belonging to the family Juncaceae is rush, the seed culture of mushroom mycelia is Mannentake mycelium, and the nutrient source is okara (soybean curd refuse).

16. The method for producing an antimicrobial agent according to claim 4, wherein the plant belonging to the family Juncaceae is rush, the seed culture of mushroom mycelia is Mannentake mycelium, and the nutrient source is okara (soybean curd refuse).

17. A water-soluble extract of the antimicrobial agent obtained by drying the culture containing the antimicrobial agent produced by the method of claim 6, extracting the dried material with water to produce an extract, and then drying the extract.

18. A water-soluble extract of the antimicrobial agent obtained by drying the culture containing the antimicrobial agent produced by the method of claim 7, extracting the dried material with water to produce an extract, and then drying the extract.

19. A powdered antimicrobial agent produced by drying and then milling the culture containing the antimicrobial agent produced by the method according to claim 6.

20. A powdered antimicrobial agent produced by drying and then milling the culture containing the antimicrobial agent produced by the method according to claim 7.

* * * * *